United States Patent
He et al.

(10) Patent No.: US 9,604,193 B2
(45) Date of Patent: Mar. 28, 2017

(54) ETHYLENE CRACKING FURNACE

(71) Applicants: CHINA PETROLEUM & CHEMICAL CORPORATION, Beijing (CN); SINOPEC Engineering Incorporation, Beijing (CN)

(72) Inventors: Xiou He, Beijing (CN); Jingkun Liu, Beijing (CN); Changli Li, Beijing (CN); Hainu Shen, Beijing (CN); Yuping Guo, Beijing (CN); Chen Shao, Beijing (CN)

(73) Assignees: CHINA PETROLEUM & CHEMICAL CORPORATION, Beijing (CN); SINOPEC ENGINEERING INCORPORATION, Beijing (CN)

( * ) Notice: Subject to any disclaimer, the term of this patent is extended or adjusted under 35 U.S.C. 154(b) by 0 days.

(21) Appl. No.: 14/925,579

(22) Filed: Oct. 28, 2015

(65) Prior Publication Data

US 2016/0045889 A1  Feb. 18, 2016

Related U.S. Application Data

(62) Division of application No. 14/235,225, filed as application No. PCT/CN2011/001239 on Jul. 28, 2011, now Pat. No. 9,205,400.

(51) Int. Cl.
*B01J 19/24* (2006.01)
*C10G 9/20* (2006.01)
(Continued)

(52) U.S. Cl.
CPC ........... *B01J 19/24* (2013.01); *B01J 19/2425* (2013.01); *C07C 4/02* (2013.01); *C07C 4/04* (2013.01);
(Continued)

(58) Field of Classification Search
CPC ... C10G 9/20; C10G 9/206; C07C 4/04; B01J 19/2415; B01J 19/2425; B01J 19/2435
See application file for complete search history.

(56) References Cited

U.S. PATENT DOCUMENTS 4,160,701 A    7/1979  Dorner et al.
4,361,478 A   11/1982  Gengler et al.
(Continued)

FOREIGN PATENT DOCUMENTS

CN    1067669 A    1/1993
CN    1260469 A    7/2000
(Continued)

*Primary Examiner* — Lessanework Seifu
(74) *Attorney, Agent, or Firm* — Novick, Kim & Lee, PLLC; Allen Xue

(57) ABSTRACT

The present disclosure provides an ethylene cracking furnace, comprising at least one radiant section provided with a bottom burner and/or a side burner, and at least one set of radiant coil arranged along a longitudinal direction of the radiant section. The radiant coil is an at least two-pass coil having an N–1 structure, wherein N is preferably a natural number from 2 to 8. A manifold is arranged at an inlet end of a downstream tube of said at least two-pass coil, and an outlet end of each upstream tube of said at least two-pass coil is connected to the manifold through a curved connector. The arrangement according to the present disclosure can effectively reduce the expansion differences between the upstream tubes and the downstream tubes, and therefore reduce the stress caused thereby. Consequently, bending of the radiant coil can be avoided, thereby extending the service life of the radiant coil.

20 Claims, 10 Drawing Sheets

(51) Int. Cl.
*C07C 4/04* (2006.01)
*F28D 7/06* (2006.01)
*C07C 4/02* (2006.01)
*F28D 21/00* (2006.01)

(52) U.S. Cl.
CPC ............... *C10G 9/20* (2013.01); *F28D 7/06* (2013.01); *B01J 2219/00083* (2013.01); *B01J 2219/00157* (2013.01); *B01J 2219/24* (2013.01); *F28D 2021/0059* (2013.01); *F28F 2210/02* (2013.01)

(56) References Cited

U.S. PATENT DOCUMENTS

| | | |
|---|---|---|
| 5,151,158 A | 9/1992 | Bowen et al. |
| 2008/0142411 A1 | 6/2008 | Barendregt et al. |
| 2012/0219466 A1 | 8/2012 | He et al. |

FOREIGN PATENT DOCUMENTS

| | | |
|---|---|---|
| CN | 1405273 A | 3/2003 |
| CN | 201520747 U | 7/2010 |
| CN | 102050696 A | 5/2011 |
| CN | 102051197 A | 5/2011 |
| CN | 102146011 A | 8/2011 |
| EP | 0305799 A1 | 3/1989 |
| EP | 0366270 A2 | 5/1990 |
| EP | 0980729 A1 | 2/2000 |
| EP | 1146105 A2 | 10/2001 |
| EP | 1561796 A1 | 8/2005 |
| JP | 10-103624 A | 4/1998 |
| WO | 2011050573 A1 | 5/2011 |

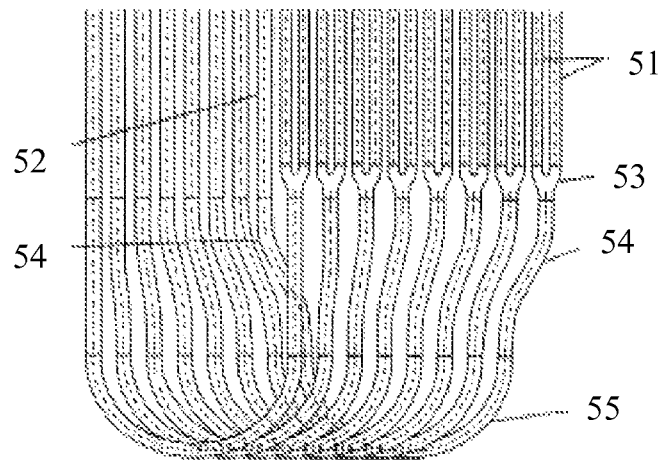
Fig. 1B PRIOR ART
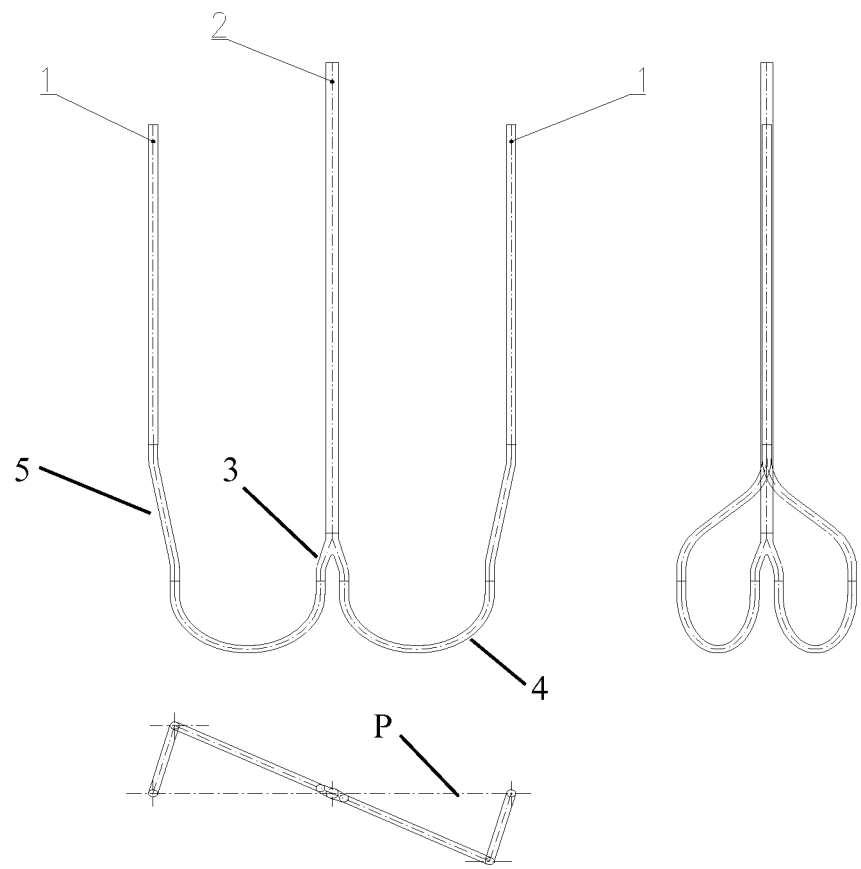
Fig. 2A
Fig. 2C
Fig. 2B

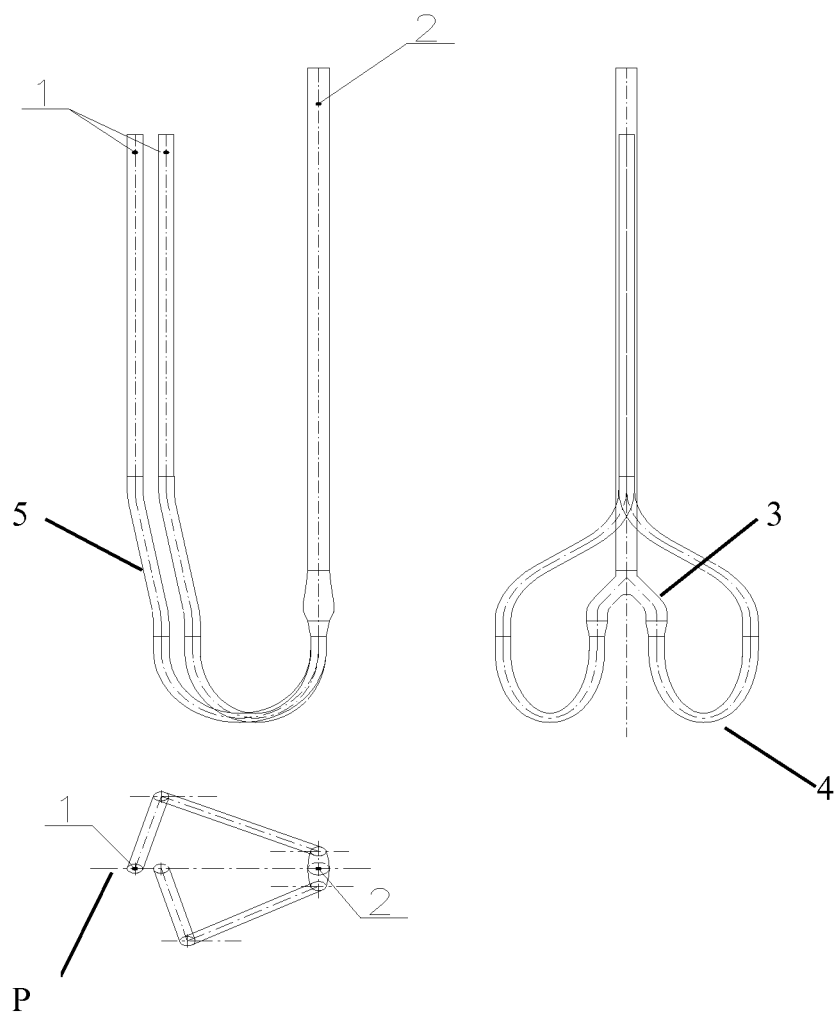

Fig. 4A
Fig. 4C
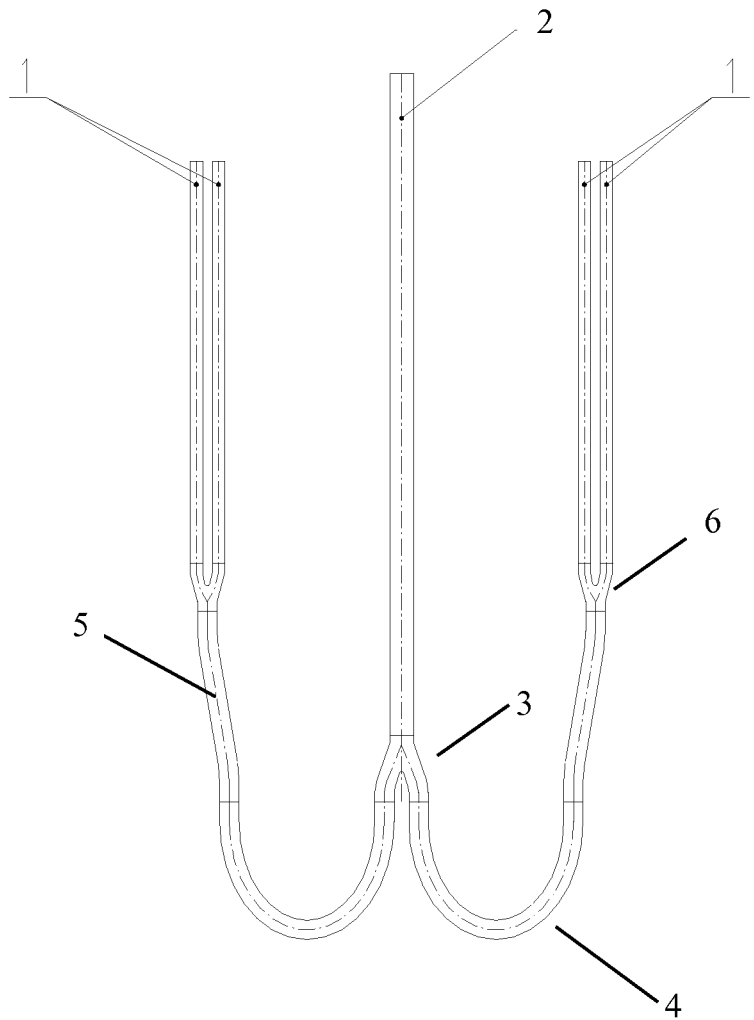
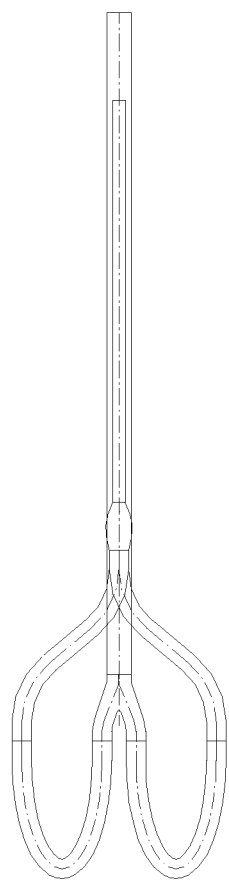
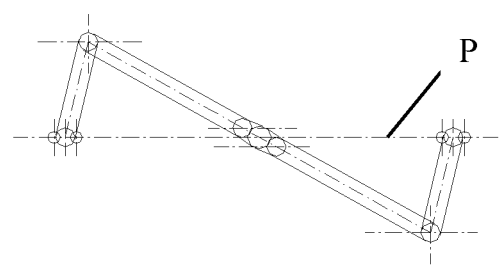
Fig. 4B

Fig. 5A
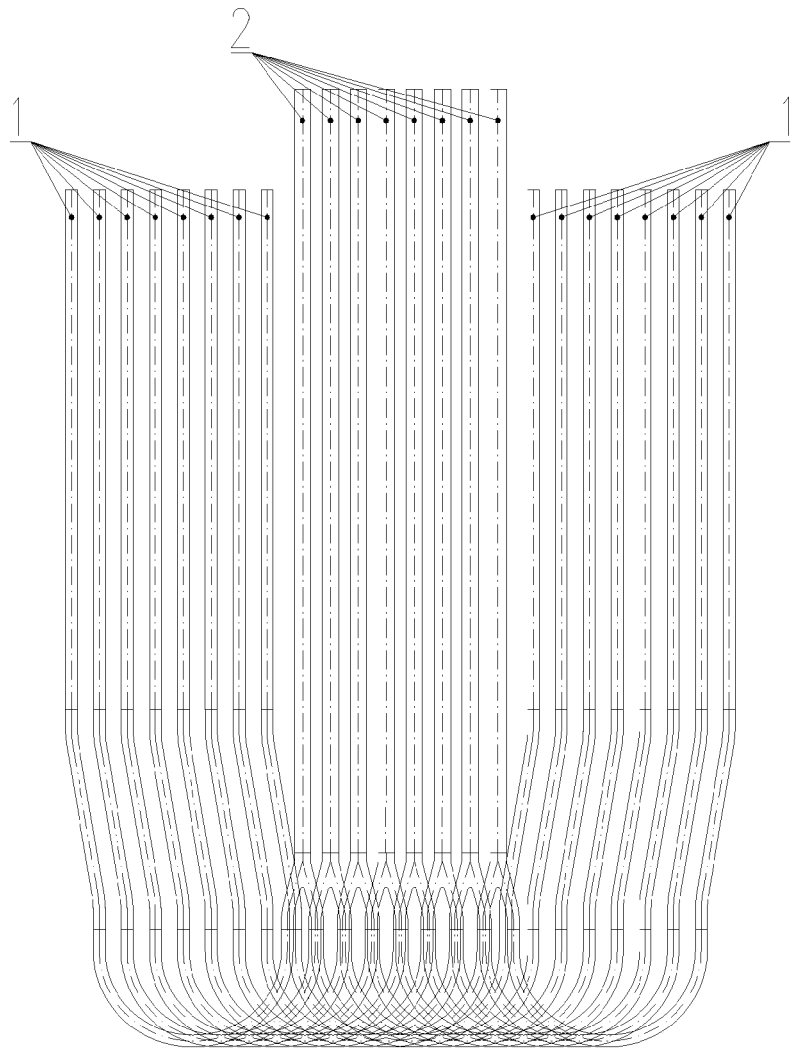
Fig. 5C
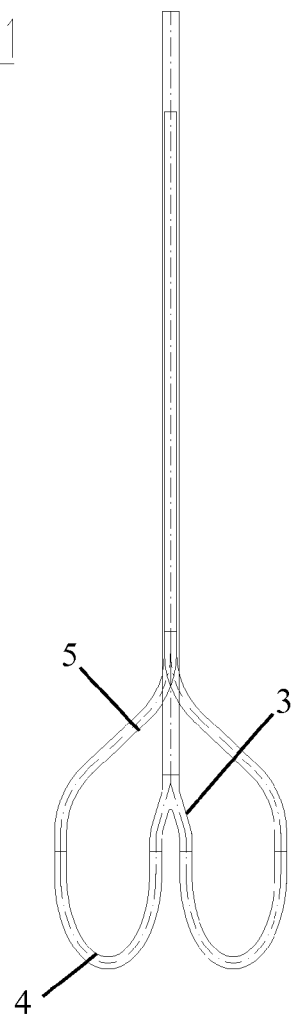
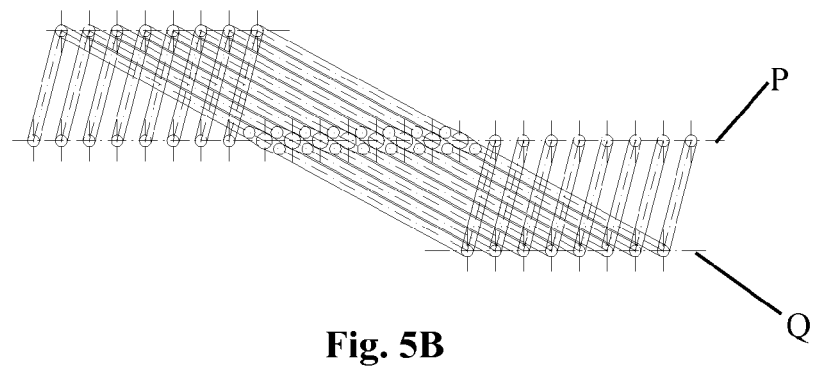
Fig. 5B

Fig. 6A
Fig. 6C
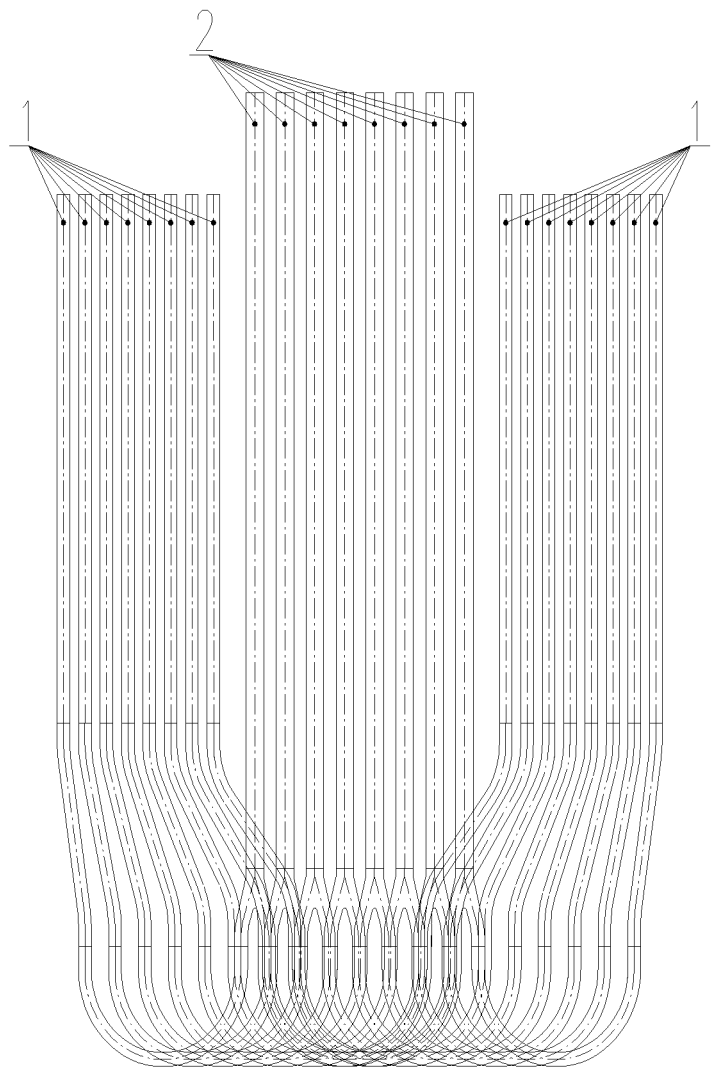
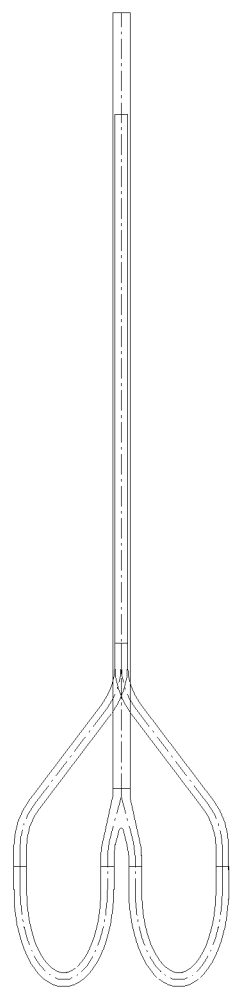
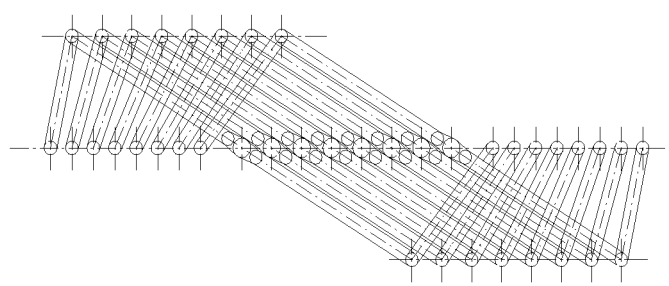
Fig. 6B

Fig. 7A
Fig. 7C
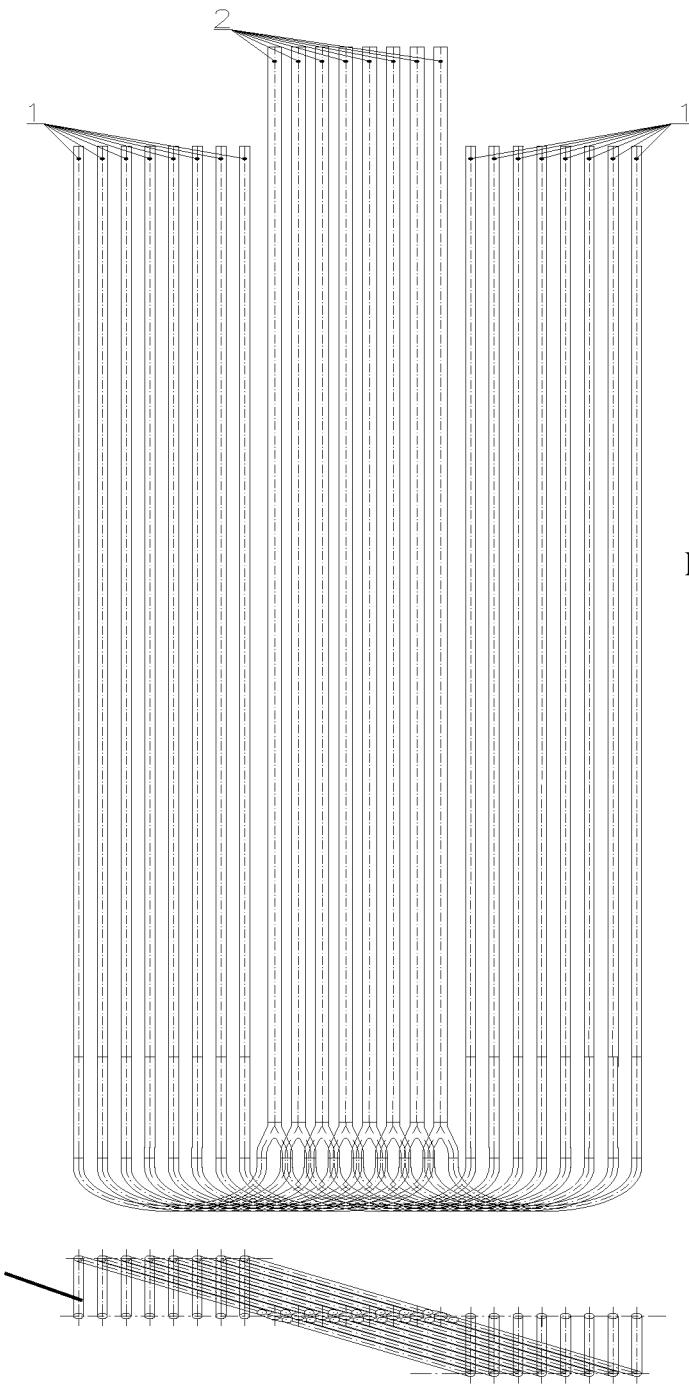
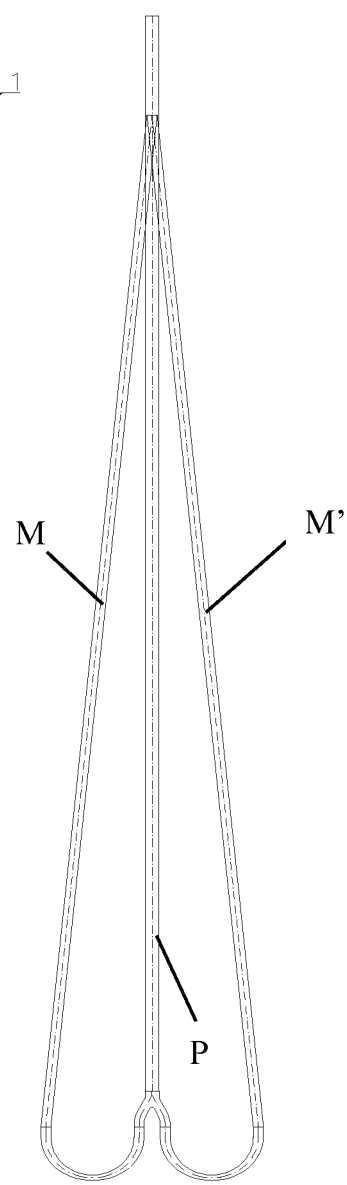
Fig. 7B

Fig. 8A
Fig. 8C
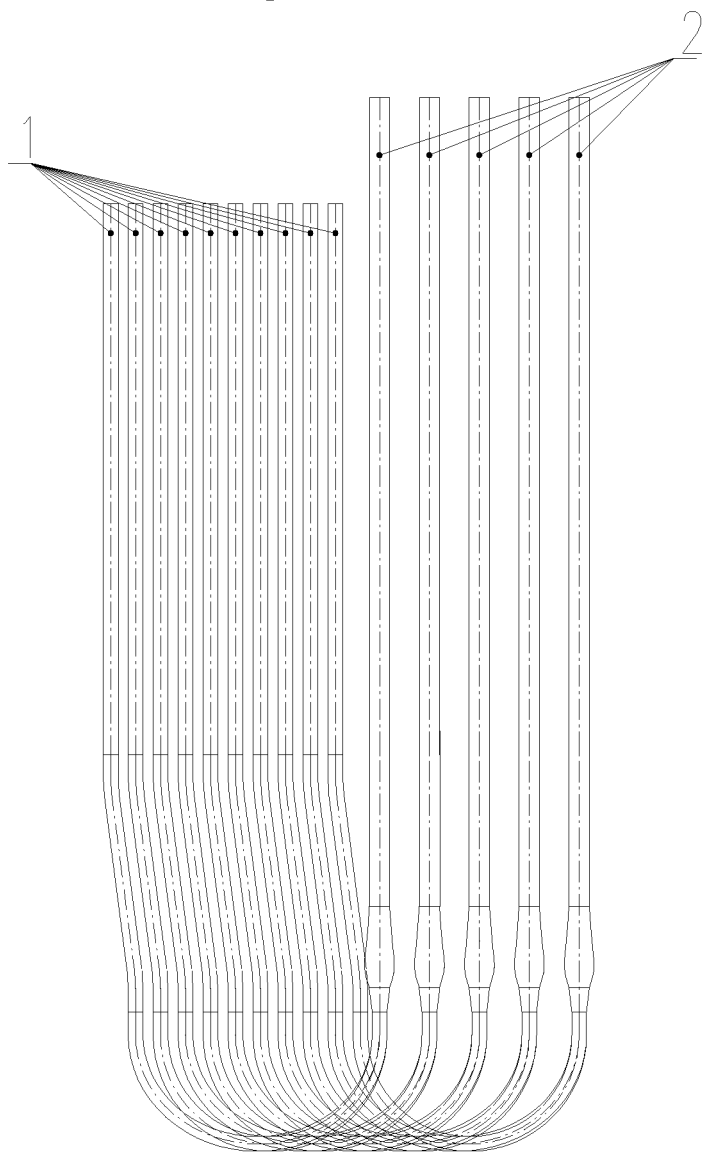
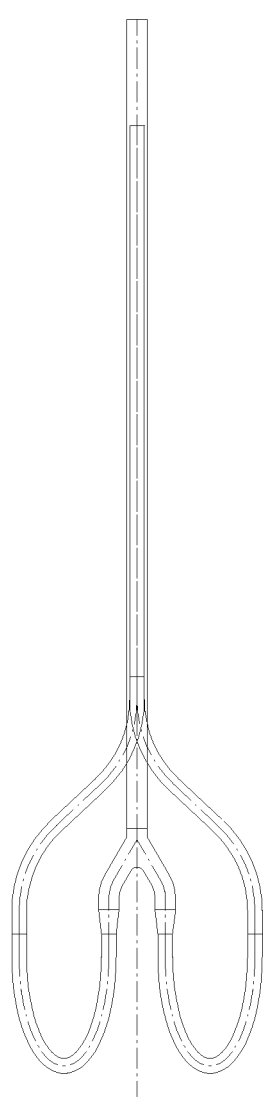
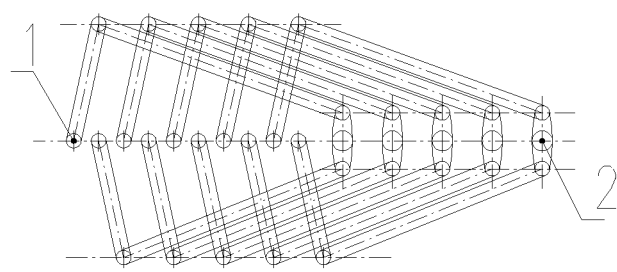
Fig. 8B

Fig. 9A  Fig. 9C  Fig. 10A  Fig. 10C
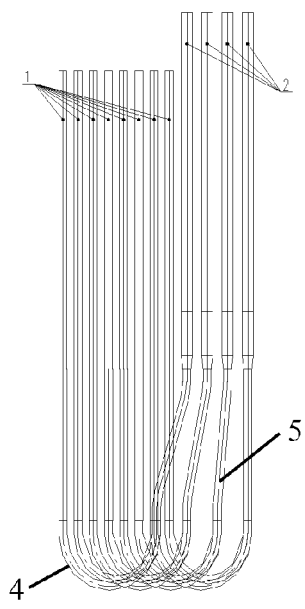
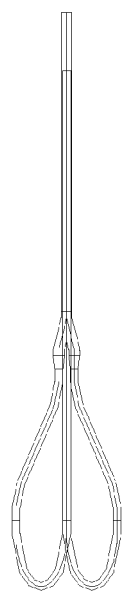
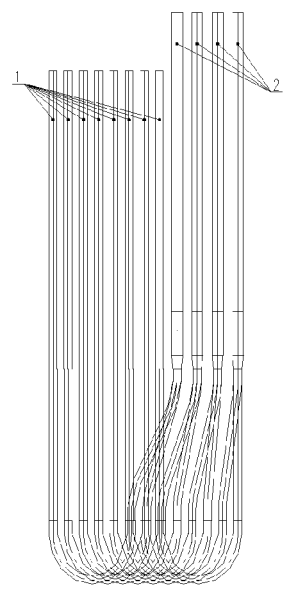
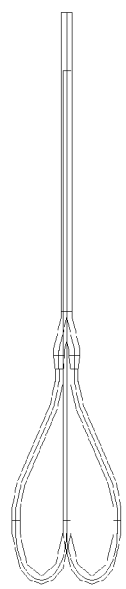
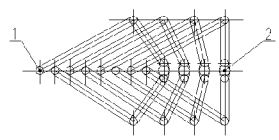
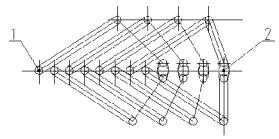
Fig. 9B  Fig. 10B Fig. 11A
Fig. 11C
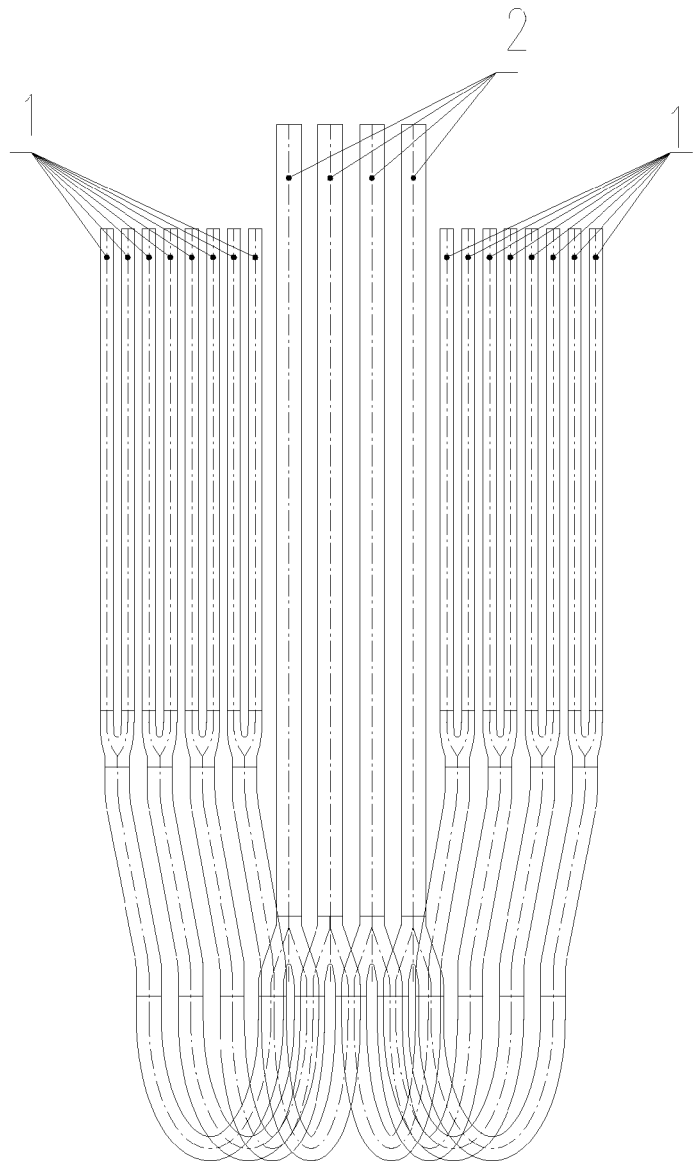
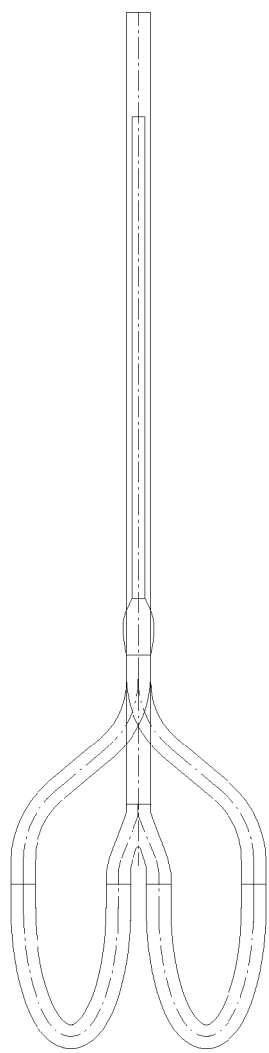
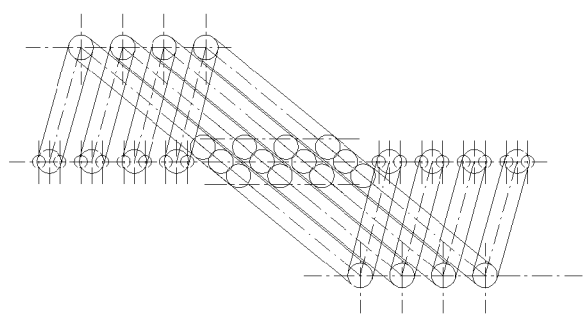
Fig. 11B

ETHYLENE CRACKING FURNACE

CROSS-REFERENCE TO RELATED APPLICATIONS

This application is a divisional application of U.S. application Ser. No. 14/235,225 filed on Mar. 18, 2014, which is a national-stage application under 35 U.S.C. §371 of PCT/CN2011/001239 filed on Jul. 28, 2011, the content of which is incorporated herein by reference in its entirety.

FIELD OF THE INVENTION

The present disclosure relates to the petrochemical engineering field, and more specifically, to a radiant coil structure of an ethylene cracking furnace used in petrochemical engineering.

BACKGROUND OF THE INVENTION

The ethylene cracking techniques used in petrochemical ethylene equipments mainly include those developed by LUMMUS Co. (USA), Stone & Webster Co. (USA), Kellog & Braun Root Co. (USA), Linde Co. (Germany), Technip KTI Co. (Netherlands), and the CBL cracking furnace developed by China Petrochemical Corporation.

FIG. 1A shows a typical ethylene cracking furnace 10, which comprises a radiant section 11, a convective section 13, and a flue section 12 located between the radiant section 11 and the convective section 13. Within the radiant section 11, a radiant coil 14 is provided in the central plane P of the radiant section 11 along the longitudinal direction thereof. In addition, the radiant section 11 is further provided with bottom burners 15 and/or side burners 16 for heating. Moreover, the ethylene cracking furnace 10 further comprises a transfer line exchanger 17, a high-pressure steam drum 18, and an induced draft fan 19, etc.

To significantly reduce the feedstock consumption, maintain a suitable run length, and have a good feedstock flexibility, nowadays a two-pass high-selectivity radiant coil with or without branches of variable diameters is used. The first-pass tube of the radiant coil is of a small diameter. Therefore, a quick temperature rise can be achieved since the specific surface area of a small-diameter tube is relatively large. The second-pass tube is of a large diameter, in order to reduce the influences on coking sensitivity. The two-pass radiant coil can be configured as 1-1 type (U type), 2-1 type, 4-1 type, 6-1 type coil, etc.

A two-pass 1-1 type coil structure, which can be matched to transfer line exchanger(s), is of a large specific surface area and good mechanical performance. The run length thereof, however, is slightly short.

For an N-1 (N>1) type coil structure, the number of tubes in the first pass is N times as more as the number of the tubes in the second pass. Therefore, the N tubes in the first pass need to be combined into one tube before being connected to a corresponding second-pass tube. EP 1146105 discloses a cracking furnace having a two-pass 2-1 type coil structure. As indicated in FIG. 1B, a two-pass radiant coil comprises first-pass tubes 51 (16 tubes) and second-pass tubes 52 (8 tubes) perpendicularly arranged in an inner chamber of a radiant section. All these tubes are located in one common plane, with all the first-pass tubes 51 arranged together, and all the second-pass tubes 52 arranged together, wherein every two first-pass tubes 51 are combined into one tube by a Y-shaped manifold 53 at a lower portion of the first-pass tubes 51 before being connected to a second-pass tube 52 via two S-shaped elbows 54 and a U-shaped elbow 55.

CN 1067669 discloses a cracking furnace having a two-pass 6-1 type coil structure, which includes 6 first-pass tubes, and one second-pass tube. Similarly, these 6 first-pass tubes are first combined into one tube via a rigid manifold arranged in a lower portion thereof, and then are connected to the second-pass tube.

In the above structures, since the number of the first-pass tubes is a plurality of times higher than the number of the second-pass tubes, when the coil is heated to expand, the second-pass tubes first expand downward, and then the first-pass tubes are dragged by the second-pass tubes to move downward also, wherein the first-pass tubes are easily bent because they are deformed under different forces. The rigidity of the manifold connected in the lower portion of the first-pass tubes prevents expansion differences thereof from being absorbed by an S-shaped tube (if any), rendering the coil easily being bent. Hence, the mechanical performance of the coil is reduced, thereby shortening the service life of the coil and the run length of the cracking furnace.

SUMMARY OF THE INVENTION

To overcome the technical defects existing in the prior art, the present disclosure discloses a new ethylene cracking furnace having a two-pass or multi-pass radiant coil, wherein a special arrangement structure of the radiant coil can reduce bending of the coil, thereby improving the mechanical performance of the coil, extending service life thereof, and prolonging the run length of the cracking furnace.

According to the present disclosure, it provides an ethylene cracking furnace, comprising at least one radiant section, which is provided with a bottom burner and/or a side burner, and at least one set of radiant coil arranged along a longitudinal direction of the radiant section, wherein the radiant coil is an at least two-pass coil having an N-1 structure, N preferably being a natural number from 2 to 8; and wherein a manifold is arranged at an inlet end of a downstream tube of said at least two-pass coil, and an outlet end of each upstream tube of said at least two-pass coil is connected to the manifold through a curved connector.

In the text of the present disclosure, the term "coil having an N-1 structure" means that in two adjacent passes of tubes, for each downstream tube there are N corresponding upstream tubes. It is easily understood, in a two-pass coil having an N-1 structure, a manifold therein can have N input ends and one output end. According to one preferred embodiment, the manifold is in the form of an invertedly Y-shaped pipe having N input ends and one output end, N equaling 2 or 4. When N equals 4, every two upstream tubes are first combined together via one Y-shaped pipe element before being connected to a curved connector. According to another embodiment, the manifold is in the form of a palm-like pipe having a plurality of input ends and one output end. In a coil having more than two passes, N-1 indicates N input ends and one output end, with all connection manners of a two-pass coil having an N-1 structure capable of being applied therein.

In one preferred embodiment, the radiant coil is a two-pass coil, wherein the upstream tube is a first-pass tube, while the downstream tube is a second-pass tube. In another embodiment, the radiant coil is a multi-pass coil having more than two passes, wherein the upstream tubes are odd-number ones such as a first-pass tube, a third-pass tube, etc., while the downstream tubes are even-numbered ones such as a second-pass tube, a fourth-pass tube, etc.

According to one embodiment, the upstream tubes are divided into two groups each with the same number of tubes respectively arranged at two sides of the downstream tube, and all of the upstream tubes and the downstream tube are arranged in a common plane.

According to one embodiment, the curved connector comprises a U-shaped elbow and an S-shaped elbow, of which one connects to a lower portion of a corresponding upstream tube, and the other connects to an inlet end of the manifold. It should be noted that the curved connector of the present disclosure can "connect" to the tube or manifold either directly or indirectly via a transition pipe, which can be selected as specifically required. In some preferred embodiments, the tube diameter of the curved connector equals the tube diameter of the upstream tube, which, for example, is especially suitable when N equals 2, or when N is larger than 2 and the manifold is in the form of a palm-like pipe.

According to one embodiment, viewed from a top view of the radiant coil, with respect to the downstream tube, corresponding S-shaped elbows are in parallel with each other, and/or corresponding U-shaped elbows are arranged in one and the same line. Preferably, all the S-shaped elbows are parallel with one another. Alternately, all the S-shaped elbows are divided into a plurality of groups, with all S-shaped elbows in each group in parallel with one another.

According to one embodiment, the upstream tubes are divided into two groups each with the same number of tubes respectively arranged at two sides of the downstream tube. In this embodiment, however, the plane in which the upstream tubes arranged at one side of the downstream tube are located and the plane in which the upstream tubes arranged at the other side of the downstream tube are no longer arranged in a common plane with the downstream tube. Instead, with respect to the plane in which the downstream tube is located, the plane in which the upstream tubes arranged at one side of the downstream tube are located is in minor relationship with the plane in which the upstream tubes arranged at the other side of the downstream tube are located. In one alternative embodiment, the upstream tubes arranged at one side of the downstream tube, the upstream tubes arranged at the other side of the downstream tube, and the downstream tube are respectively in three planes parallel with one another.

According to the present disclosure, the upstream tubes can be all arranged at one and the same side of the downstream tube with all the upstream tubes and the downstream tube positioned in a common plane. According to one embodiment, the curved connectors of two adjacent upstream tubes are respectively located at two sides of the plane in which the tubes are located. In one embodiment, the upstream tubes do not have a common plane with the downstream tube, but are respectively arranged in two parallel planes, which is in parallel with the plane in which the downstream tube is arranged. In another embodiment, the upstream tubes are respectively arranged in two planes in minor relationship with each other with respect to the plane in which the downstream tube is located.

Comparing with the prior art, the present disclosure brings about the following advantageous technical effects:

(1) Since the first-pass tube is combined with the second-pass tube at the lower portion thereof, and S-shaped elbows and U-shaped elbows are used, the stress caused by expansion differences among the first-pass tubes that exist in 2-1 type, 4-1 type, and other types of coils can be effectively reduced. Consequently, bending of the radiant coil can be avoided, thereby extending the service life of the radiant coil.

(2) The S-shaped elbows and U-shaped elbows of the upstream tubes have smaller tube diameters when the upstream tubes are combined at the lower portion the downstream tube than when the upstream tubes are combined at the lower portion of the upstream tubes. Therefore, the upstream tubes have better flexibility, which facilitates absorption of heat expansion differences in two adjacent passes of tubes, thus avoiding bending of the tubes and finally extending service life of the radiant coil.

(3) A small tube diameter of the first-pass tube results in a high specific surface area thereof. Therefore, when the first-pass coil is extended, the specific surface area of the whole coil would be increased, which facilitates extension of the run length of the cracking furnace at the same cracking depth, and improves olefin yield at the same run length.

BRIEF DESCRIPTION OF THE DRAWINGS

FIG. 1B shows a typical two-pass 2-1 type coil structure according to the prior art;

FIGS. 2A, 2B, and 2C respectively show a front view, a top view, and a side view of one embodiment of a two-pass 2-1 type coil structure according to the present disclosure, wherein first-pass tubes are divided into two groups with the same number of tubes in each group respectively arranged at two sides of a second-pass tube;

FIGS. 3A, 3B, and 3C respectively show a front view, a top view, and a side view of another embodiment of the two-pass 2-1 type coil structure according to the present disclosure, wherein all the first-pass tubes are arranged at one and the same side of the second-pass tube;

FIGS. 4A, 4B, and 4C respectively show a front view, a top view, and a side view of one embodiment of a two-pass 4-1 type coil structure according to the present disclosure;

FIGS. 5A to 7C show front views, top views, and side views of three variations of the two-pass 2-1 type coil structure according to the present disclosure, wherein the first-pass tubes are divided into two groups with the same number of tubes in each group respectively arranged at the two sides of the second-pass tube, or all the first-pass tubes are arranged at one and the same side of the second-pass tube;

FIGS. 8A to 10C show front views, top views, and side views of three variations of the two-pass 2-1 type coil structure according to the present disclosure, wherein all the first-pass tubes are arranged at one and the same side of the second-pass tube; and FIGS. 11A to 11C respectively show a front view, a top view, and a side view of one variation of the two-pass 4-1 type coil structure according to the present disclosure.

Figure 1A:
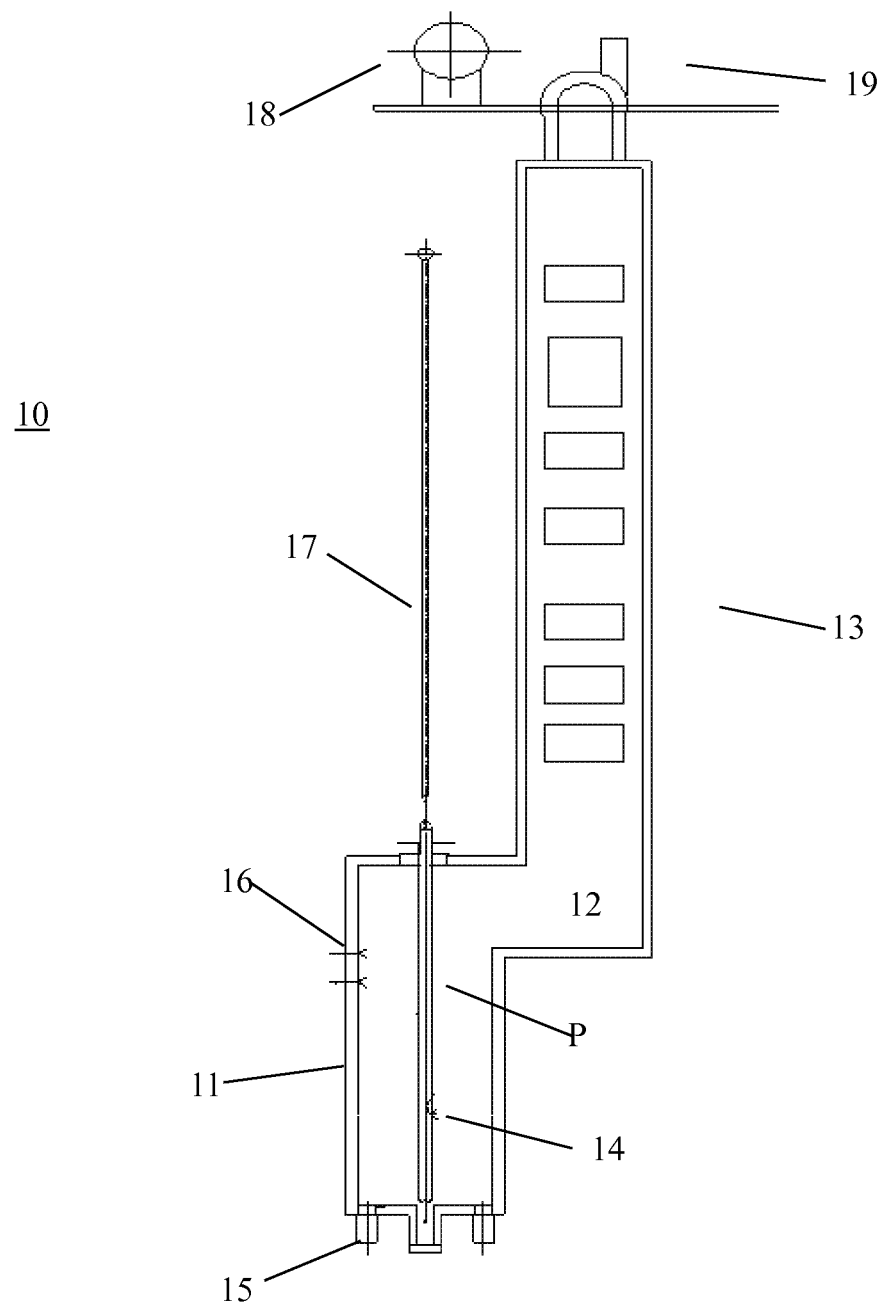
FIG. 1A shows a typical ethylene cracking furnace according to the prior art.

In the accompanying drawings, the same component or structure is indicated by the same reference sign.

DETAILED DESCRIPTION OF THE EMBODIMENTS

In the following the present disclosure will be discussed in details with reference to the accompanying drawings. It should be noted that the present disclosure aims to provide improvements on radiant coil in the radiant section of the ethylene cracking furnace. Other structures in the ethylene cracking furnace, such as the convective section, the transfer line exchanger and the like, are already known in the prior art. For example, the transfer line exchanger suitable for the present disclosure can be a double-coil transfer line exchanger (such as a linear transfer line exchanger, U-type transfer line exchanger, and the first level of a two-level transfer line exchanger, etc.), conventional boiler, etc. Moreover, the two-pass radiant coil of the present disclosure can be mainly suitable for cracking liquid material, but also suitable for cracking gas material. In contrast, the multiple-pass radiant coil of the present disclosure can be mainly suitable for cracking gas material, but also suitable for cracking liquid material. In addition, both of the two-pass radiant coil and the multiple-pass radiant coil of the present disclosure can be used in building new cracking furnaces or reconstructing existing cracking furnaces. These are known to one ordinarily skilled in the art, and thus their details thereof are omitted here.

FIGS. 2A, 2B, and 2C illustrate a first embodiment according to the present disclosure, which involves a two-pass 2-1 type coil structure. As shown in the Figures, the two-pass 2-1 type coil according to the embodiment comprises two first-pass tubes 1 and one second-pass tube 2. The front view, i.e., FIG. 2A indicates that said two first-pass tubes 1 are respectively arranged at two sides of the second-pass tube 2. Moreover, the three tubes have three center lines positioned in a common plane P (see FIG. 2B).

According to the present disclosure, a lower end (i.e., an input end) of the second-pass tube 2 is provided with a manifold 3, which is used for combining the two first-pass tubes 1 and connecting the same to the second-pass tube 2. In the specific embodiment, the manifold 3 is in the form of an invertedly U-shaped pipe, i.e., having two input ends and one output end, wherein the output end is connected to the lower end of the second-pass tube 2. The two first-pass tubes 1 are respectively connected to the two input ends of the manifold 3 via two respective curved connectors (each consisting of an S-shaped elbow 5 and a U-shaped elbow 4) arranged at lower ends of the two first-pass tubes 1 (i.e., output ends thereof). It can be easily understood, for an N–1 type coil structure (N>2), the manifold can be designed to have N input ends and one output end, i.e., in the form of a palm. In addition, the curved connector can be connected to the two input ends of the manifold 3 via a transition pipe to satisfy the requirements of process and mechanical design. In one specific embodiment, the transition pipe, which can be a straight pipe or an elbow, has the same tube diameter as the curved connector.

With the arrangement of the manifold 3 as a rigid connecting structure at the lower end of the second-pass tube 2 instead of at the lower end of the first-pass tubes 1, stress caused by the expansion differences between the first-pass tubes 1 and the second-pass tube 2 under heating, and stress unbalances caused by expansion differences between the first-pass tubes 1 can be absorbed by the S-shaped elbow 5 and the U-shaped elbow 4 arranged at the lower end of the first-pass tubes 1. Hence, deformation is reduced, thus extending the service life of the coil.

Furthermore, according to the present disclosure, the S-shaped elbow 5 and the U-shaped elbow 4 are connected to the lower end of the first-pass tubes 1 and have the same tube diameter as the first-pass tubes 1, thereby essentially extending the length of the first-pass tubes 1. Such being the case, the specific surface area of the tubes is increased, which is advantageous for extending the run length of the cracking furnace under the same cracking depth, and for improving product yield under the same run length of the cracking furnace. Besides, because the curved connector has the same tube diameter as the first-pass tubes, the flexibility thereof is improved, which facilitates elimination of thermal stress, thereby reducing deformation of the tubes and extending service life thereof.

Advantageously, the S-shaped elbow 5 and U-shaped elbow 4 connected to the lower end of the first-pass tube 1 which is arranged at a left side of the second-pass tube 2 (see FIG. 2A), and the S-shaped elbow 5 and U-shaped elbow 4 connected to the lower end of the other first-pass tube 1 which is arranged at a right side of the second-pass tube 2 (see FIG. 2A) are respectively located at two sides of the plane P (see FIGS. 2B and 2C). This arrangement facilitates more homogeneous absorption of deformation caused by the thermal stress, thus further reducing the temperature on the surface of the tubes and extending the service life thereof.

In one preferred embodiment, as indicated in FIG. 2B, the top view, the respective S-shaped elbows 5 of the two first-pass tubes 1 are in parallel with each other, while the respective U-shaped elbows 4 of the two first-pass tubes 1 are in one and the same line. More preferably, with respect to the center line of the second-pass tube 2, the S-shaped elbow 5 and U-shaped elbow 4 of the first-pass tube 1 located at one side of the plane P are in 180° rotation symmetry with the S-shaped elbow 5 and U-shaped elbow 4 of the first-pass tube 1 located at the other side of the plane P.

Moreover, as required in the process or mechanical design, a straight pipe of certain length and of the same tube diameter as the first-pass tubes can be provided between the manifold 3 and the curved connector.

According to one variation of the first embodiment, the first-pass tubes 1 and the second-pass tube 2 can be arranged at different planes, wherein the curved connector can merely comprises the U-shaped elbow 4, while the S-shaped elbow 5 can be omitted.

Other embodiments according to the present disclosure will be explained in the following. For the sake of simplicity, only features or components that are different from those in the embodiment as explained above and the functions thereof will be discussed, while the same features or components or the functions thereof will not be repeated.

FIGS. 3A, 3B, and 3C show a second embodiment according to the present disclosure. The second embodiment distinguishes from the first embodiment in that both of the two first-pass tubes 1 are arranged at one and the same side of the second-pass tube 2 (see the front view FIG. 3A). This arrangement can also realize the advantages as stated in the first embodiment, and is applicable in some cracking furnaces of specific structures. In the second embodiment, the S-shaped elbow 5 and U-shaped elbow 4 connected to the lower end of one of the first-pass tubes 1, and the S-shaped elbow 5 and U-shaped elbow 4 connected to the lower end of the other of the first-pass tubes 1 are still respectively arranged at the two sides of the plane P in which all the three tubes are located (see FIGS. 3B and 3C).

In one embodiment, viewed form a side view, a group of the S-shaped elbow 5 and U-shaped elbow 4 is in minor relationship with another group of the S-shaped elbow 5 and U-shaped elbow 4 with respect to the plane P (see FIG. 3C). In one embodiment not shown, however, both groups of curved connectors may not be in minor relationship with each other, in order to ensure the same length and weight between the elbows at the two sides.

Similarly, when the first-pass tubes 1 and the second-pass tube 2 are not arranged in a common plane, the curved connector can only comprise the U-shaped elbow 4, while the S-shaped elbow 5 can be omitted.

FIGS. 4A, 4B, and 4C show a third embodiment according to the present disclosure. The third embodiment is different from the first embodiment in that the third embodiment involves a two-pass 4-1 type coil structure. As demonstrated by the Figures, both sides of the second-pass tube 2 are provided with two first-pass tubes 1. The two first-pass tubes 1 in either side are first combined into one pipe via a manifold 6, then connected to the S-shaped elbow 5 and the U-shaped elbow 4, and finally connected to the manifold 3 positioned at the lower end of the second-pass tube 2. In the embodiment, the manifold 6 is in the form of a Y-shaped pipe element having two input ends and one output end. In addition, according to the requirements in the process and mechanical design, the two first-pass tubes 1 in either side can first be combined into one pipe via one manifold 6, then connected to the S-shaped elbow 5 and the U-shaped elbow 4 by connecting to one straight pipe, and finally connected to the manifold 3 arranged at the lower end of the second-pass tube 2 via one transition pipe (i.e., a straight pipe or an elbow).

It can be easily understood that in one embodiment not shown, the manifold 6 can be omitted. Meanwhile, the manifold 3 can be modified to have four input ends and one output end. In this case, the four first-pass tubes 1 can be directly connected to the four input ends via necessary elbows (i.e., U-shaped elbows 4 and S-shaped elbows 5), or via a transition pipe (i.e., a straight pipe or an elbow).

FIGS. 5A, 5B, and 5C show a fourth embodiment according to the present disclosure. The fourth embodiment is still a two-pass 2-1 type coil structure, which is designed in the same way as the first embodiment except that it comprises 8 second-pass tubes 2 arranged together side by side, and 16 first-pass tubes 1 which are divided into two groups with 8 tubes in each group respectively arranged at the two sides of the second-pass tubes 2. The structure of the fourth embodiment is equivalent to a structure including 8 coils of the first embodiments arranged together in parallel with one another. As shown in FIG. 5B, all the 16 S-shaped elbows 5 are in parallel with one another. Furthermore, for each second-pass tube 2, the corresponding two U-shaped elbows 4 are placed in one and the same line. Preferably, the corresponding U-shaped elbows 4 of each second-pass tube 2 are in parallel with one another.

In addition, preferably, at the two sides of the plane P, all connecting areas of the S-shaped elbows 5 and the U-shaped elbows 4 are located in a common plane Q, which is in parallel with the plane P.

FIGS. 6A, 6B, and 6C show a fifth embodiment according to the present disclosure. The fifth embodiment is substantially the same as the fourth embodiment except that not all the 16 S-shaped elbows 5 are in parallel with one another. Instead, they are divided into several groups and all elbows in a group are in parallel with one another. As indicated in the Figures, the S-shaped elbows 5 are grouped with an outer elbow and an inner elbow, and the two S-shaped elbows 5 in each group are parallel with each other.

FIGS. 7A, 7B, and 7C show a sixth embodiment according to the present disclosure. The sixth embodiment is substantially the same as the fourth embodiment except that the first-pass tubes 1 are not arranged to have a common plane with the second-pass tube 2. As illustrated in FIG. 7C, the side view, a plane M in which eight first-pass tubes 1 are located at one side of the second-pass tube 2, and a plane M' in which the other eight first-pass tubes 1 are located at the other side of the second-pass tube 2, form an acute angle respectively with respect to the plane P in which the second-pass tube 2 is located. Preferably, the planes M and M' are in mirror relationship with respect to the plane P. In addition, as shown in FIG. 7B, the top view, each of the first-pass tubes 1 has an axis line L perpendicular to the plane P in which the second-pass tube 2 is located. It can be easily understood, in one specific embodiment, the planes M, M' can be in parallel with the plane P. That is, either the plane M or M' defines an angle of zero with the plane P. Furthermore, it would easily occur to one skilled in the art that this structure is applicable to any cases in which all the first-pass tubes are positioned at one and the same side of the second-pass tube 2 (for example in the second embodiment of the present disclosure).

FIGS. 8A, 8B, and 8C show a seventh embodiment according to the present disclosure. The seventh embodiment is substantially the same as the second embodiment except that it comprises five second-pass tubes 2 arranged together side by side, and 10 first-pass tubes 1 arranged at one and the same side of the second-pass tubes 2. The structure of this embodiment is equivalent to five coils as illustrated in the first embodiment arranged together in parallel with one another. As shown in FIG. 8B, the S-shaped elbows 5 and U-shaped elbows 4 connected to the lower end of the first-pass tubes are staggered with each other with respect to the plane P in which the tubes are located, i.e., the S-shaped elbow 5 and U-shaped elbow 4 connected to a first tube of the first-pass tubes are arranged at one side of the plane P (an upper portion in the top view), while the S-shaped elbow 5 and U-shaped elbow 4 connected to a second tube of the first-pass tubes are arranged at the other side of the plane P (a lower portion in the top view), so on and so forth. Besides, all the S-shaped elbows 5 at the upper portion of the top view are in parallel with one another, and all the U-shaped elbows 4 thereof are also in parallel with one another. And all the S-shaped elbows 5 at the lower portion of the top view are in parallel with one another, and all the U-shaped elbows 4 thereof are also in parallel with one another.

Additionally, in this embodiment, viewed from the side view (see FIG. 8C), the S-shaped elbows 5 and U-shaped elbows 4 respectively arranged at the two sides of the plane P are in minor relationship with each other with respect to the plane P. In one embodiment not shown, however, the side projections thereof are not in symmetry in order to ensure the same pipe length of the two curved connectors connected to one and the same manifold.

FIGS. 9A, 9B, and 9C show an eighth embodiment according to the present disclosure. The eighth embodiment is substantially the same as the seventh embodiment except that the lower end of the first-pass tube 1 is first connected to the U-shaped elbow 4, then to the S-shaped elbow 5, and finally to the manifold 3. That is, the layout order of the U-shaped elbow 4 and S-shaped elbow 5 are different from that in any one of the preceding embodiments. Preferably, the S-shaped elbows 5 respectively arranged at the two sides of the plane P in which the tubes are located are in mirror relationship with respect to the plane P in the top view. Still preferably, the pipe length of the connector connecting to the first-pass tube is the same as that of connecting to the second-pass tube (see FIG. 9B).

FIGS. 10A, 10B, and 10C show a ninth embodiment according to the present disclosure. The ninth embodiment is substantially the same as the eighth embodiment except that all the U-shaped elbows are the same as one another, and the S-shaped elbows respectively positioned at the two sides of the plane P in which the tubes are located are not in mirror relationship with respect to plane P.

FIGS. 11A, 11B, and 11C show a tenth embodiment according to the present disclosure. The tenth embodiment, which is a two-pass 4-1 type coil structure, is substantially the same as the first embodiment except that it comprises four second-pass tubes 2 arranged together in parallel with one another, and 16 first-pass tubes 1 which are divided into two groups each group with eight tubes respectively arranged at the two sides of the second-pass tubes 2. The structure of this embodiment is equivalent to four coils of the third embodiment arranged together in parallel with one another.

According to the present disclosure, an inner diameter of the first-pass tube 1 can be in the range from 40 to 65 mm, an inner diameter of the second-pass tube can be in the range from 55 to 130 mm, and an inner diameter of the connector connecting the first-pass and the second-pass tubes can be in the range from 40 to 90 mm. Furthermore, the length of the first-pass tube 1 generally can be selected as within the range from 8 to 18 m, while the length of the second-pass tube 2 can be selected within the range from 6 to 14 m. The above parameters, and other parameters concerning the length and inner diameter of tubes and connectors are not limited in the above ranges but can be selected as specifically required, which is well known by one skilled in the art.

In one preferred embodiment, an intensified heat transfer member, such as the twisted tube as disclosed in CN 1260469, can be further provided in the radiant coil structure, in order to facilitate absorption of radiant heat.

Although the cracking furnace of the present disclosure is exemplarily described with the two-pass radiant coil structure, it however be understood that the present disclosure can also be used in a radiant coil structure having more than two passes. For example, in an 8-4-2-1 type four-pass coil structure, a manifold can be provided at a lower end of a second-pass or a fourth-pass tube. One skilled in the art would easily think of the above after reading the present disclosure.

Moreover, although in the foregoing the present disclosure is described with reference to one set of radiant coil arranged in one cracking furnace, it can be understood that a plurality of sets of radiant coils can be arranged in one single cracking furnace, dependent on the actual requirements. When one cracking furnace is provided with a plurality of radiant coils as described in the above embodiments, the radiant coils can be arranged in sequence. Alternatively, the plurality of radiant coils can be arranged in the form of manifolds. In this case, the coils should be arranged in a mirror-symmetric way.

Although the present disclosure is described in details with reference to some embodiments, it would be apparent to one skilled in the art that modifications and variations may be made to some features/components/structures of the present disclosure without departing from the spirit or scope of the invention. In particular, the features disclosed in one embodiment can be combined with those disclosed in other embodiments in arbitrary ways unless the combinations may cause conflicts. It is intended that the present disclosure covers all the modifications and variations thereof provided they come within the scope of the appended claims and their equivalents.

The invention claimed is:

1. An ethylene cracking furnace, comprising:
    one or more radiant sections, at least one radiant section comprising a bottom burner and/or a side burner, and
    one or more radiant coils arranged along a longitudinal direction of the radiant section,
    wherein the radiant coil is an at least two-pass coil having one downstream tube and N upstream tubes in two adjacent passes, N being an even number from 2 to 8;
    a manifold is connected to an inlet end of the downstream tube, and to an outlet end of each of the N upstream tubes through a curved connector, and
    the inlet end of the downstream tube is located below an outlet end thereof, so that the manifold is arranged below the downstream tube.

2. The ethylene cracking furnace according to claim 1, wherein all upstream tubes are arranged on a same side of the downstream tube.

3. The ethylene cracking furnace according to claim 1, wherein the manifold is in the form of a Y-shaped pipe having two or four input ends and one output end.

4. The ethylene cracking furnace according to claim 1, wherein all upstream tubes and the downstream tube are arranged in a same plane.

5. The ethylene cracking furnace according to claim 2, wherein viewed from a top view of the radiant coil, the curved connectors of two adjacent upstream tubes are respectively located on two different sides of a plane where the tubes reside.

6. The ethylene cracking furnace according to claim 5, wherein the curved connectors of two adjacent upstream tubes have a same length.

7. The ethylene cracking furnace according to claim 1, wherein the curved connector comprises a U-shaped elbow and an S-shaped elbow, of which one connects to an outlet end of a corresponding upstream tube and the other connects to an inlet end of the manifold.

8. The ethylene cracking furnace according to claim 7, wherein each S-shaped elbow is connected to the outlet end of a corresponding upstream tube, and each U-shaped elbow is connected to the inlet end of the manifold, and
    the U-shaped elbows on either side of a plane where the tubes reside are parallel to each other.

9. The ethylene cracking furnace according to claim 7, wherein each S-shaped elbow is connected to the outlet end of a corresponding upstream tube, and each U-shaped elbow is connected to the inlet end of the manifold, and
    the S-shaped elbows on a same side of a plane where the tubes reside are parallel to each other.

10. The ethylene cracking furnace according to claim 7, wherein each S-shaped elbow is connected to the inlet end of the manifold, and each U-shaped elbow is connected to the outlet end of a corresponding upstream tube.

11. The ethylene cracking furnace according to claim 10, wherein the S-shaped elbows arranged respectively on two different sides of a plane where the tubes reside are in a mirror relationship across the plane.

12. The ethylene cracking furnace according to claim 10, wherein the U-shaped elbows arranged on a same side of a plane where the tubes reside are parallel to each other and have a same shape.

13. The ethylene cracking furnace according to claim 1, wherein all the upstream tubes are arranged in two planes respectively, which are in a minor relationship with respect to a plane where the downstream tube resides.

14. The ethylene cracking furnace according to claim 13, wherein the N upstream tubes are evenly divided into a first group and a second group, respectively arranged at two different side of a plane where the downstream tube resides, and a plane where the upstream tubes arranged at one side of the downstream tube reside and a plane where the upstream tubes arranged at the other side of the downstream tube reside are in a minor relationship across a plane where the downstream tube resides.

15. The ethylene cracking furnace according to claim 14, wherein the plane where the upstream tubes arranged at one side of the downstream tube reside, the plane where the upstream tubes arranged at the other side of the downstream tube reside, and the plane where the downstream tube resides are parallel to one another.

16. The ethylene cracking furnace according to claim 2, wherein the curved connector comprises a U-shaped elbow and an S-shaped elbow, of which one connects to the outlet end of a corresponding upstream tube and the other connects to an inlet end of the manifold.

17. The ethylene cracking furnace according to claim 16, wherein the S-shaped elbows arranged respectively on two different sides of a plane where the tubes reside are in a mirror relationship across the plane.

18. The ethylene cracking furnace according to claim 1, wherein a tube diameter of the curved connector equals a tube diameter of the upstream tube.

19. The ethylene cracking furnace according to claim 1, wherein the radiant coil is a two-pass coil, the upstream tube being the first-pass tube and the downstream tube being the second-pass tube.

20. The ethylene cracking furnace according to claim 1, wherein the radiant coil has more than two passes, the upstream tubes being used for odd-numbered passes while the downstream tubes being used for even-numbered passes.

* * * * *